United States Patent
Khoo

(10) Patent No.: US 11,390,743 B2
(45) Date of Patent: Jul. 19, 2022

(54) ELASTOMERIC COMPOSITION FOR AN ELASTOMERIC ARTICLE

(71) Applicant: Inoova Material Science Sdn Bhd, Selangor Darul Ehsan (MY)

(72) Inventor: Siong Hui Khoo, Selangor Darul Ehsan (MY)

(73) Assignee: INOOVA MATERIAL SCIENCE SDN BHD, Selangor Darul Ehsan (MY)

( * ) Notice: Subject to any disclaimer, the term of this patent is extended or adjusted under 35 U.S.C. 154(b) by 0 days.

(21) Appl. No.: 16/472,613

(22) PCT Filed: Dec. 20, 2017

(86) PCT No.: PCT/MY2017/050081
§ 371 (c)(1),
(2) Date: Jun. 21, 2019

(87) PCT Pub. No.: WO2018/117812
PCT Pub. Date: Jun. 28, 2018

(65) Prior Publication Data
US 2020/0087510 A1 Mar. 19, 2020

(30) Foreign Application Priority Data
Dec. 23, 2016 (MY) .................... PI 2016704795

(51) Int. Cl.
| | | |
|---|---|---|
| C08L 75/04 | (2006.01) | |
| A61B 42/10 | (2016.01) | |
| A41D 19/00 | (2006.01) | |
| A61F 6/04 | (2006.01) | |
| C08J 5/02 | (2006.01) | |
| C08J 7/12 | (2006.01) | |
| C08K 5/00 | (2006.01) | |
| C08K 5/13 | (2006.01) | |
| C08K 5/205 | (2006.01) | |
| C08K 5/372 | (2006.01) | |
| C08K 5/46 | (2006.01) | |
| C08L 7/02 | (2006.01) | |
| C08L 11/02 | (2006.01) | |
| C08L 25/10 | (2006.01) | |
| C08L 27/18 | (2006.01) | |
| C08L 71/02 | (2006.01) | |
| C08L 83/04 | (2006.01) | |

(52) U.S. Cl.
CPC .......... *C08L 75/04* (2013.01); *A41D 19/0055* (2013.01); *A61B 42/10* (2016.02); *A61F 6/04* (2013.01); *C08J 5/02* (2013.01); *C08J 7/12* (2013.01); *C08K 5/005* (2013.01); *C08K 5/0025* (2013.01); *C08K 5/13* (2013.01); *C08K 5/205* (2013.01); *C08K 5/3725* (2013.01); *C08K 5/46* (2013.01); *C08L 7/02* (2013.01); *C08L 11/02* (2013.01); *C08L 25/10* (2013.01); *C08L 27/18* (2013.01); *C08L 71/02* (2013.01); *C08L 83/04* (2013.01); *C08L 2201/54* (2013.01); *C08L 2203/02* (2013.01); *C08L 2207/04* (2013.01); *Y10T 428/13* (2015.01); *Y10T 428/1352* (2015.01); *Y10T 428/1386* (2015.01)

(58) Field of Classification Search
CPC .. C08L 75/04; C08L 7/02; C08L 11/02; C08L 25/10; C08L 27/18; C08L 71/02; C08L 83/04; C08L 9/04; C08L 9/10; C08L 9/00; C08L 2201/54; C08L 2203/02; C08L 2207/04; A61B 42/10; A41D 19/0055; A61F 6/04; C08J 5/02; C08J 7/12; C08J 7/02; C08J 2321/02; C08J 2375/04; C08J 2483/04; C08K 5/0025; C08K 5/005; C08K 5/13; C08K 5/205; C08K 5/3725; C08K 5/46; C08K 5/541; C08K 5/02; Y10T 428/13; Y10T 428/1386; Y10T 428/1352
See application file for complete search history.

(56) References Cited

U.S. PATENT DOCUMENTS

| | | | |
|---|---|---|---|
| 3,992,221 A | 11/1976 | Homsy et al. | |
| 5,232,691 A | 8/1993 | Lemole | |
| 5,399,400 A * | 3/1995 | Nile | A61L 31/041 |
| | | | 2/168 |
| 5,571,219 A | 11/1996 | Gorton | |
| 6,391,409 B1 | 5/2002 | Yeh et al. | |
| 2004/0115444 A1 | 6/2004 | Janssen et al. | |
| 2004/0253459 A1* | 12/2004 | Triebes | A41D 19/0058 |
| | | | 428/447 |
| 2007/0104904 A1* | 5/2007 | Hamann | B32B 25/00 |
| | | | 428/35.7 |
| 2010/0004394 A1* | 1/2010 | Higaki | C08L 25/16 |
| | | | 525/72 |
| 2012/0246799 A1* | 10/2012 | Khoo | C08K 3/22 |
| | | | 2/168 |
| 2014/0165263 A1 | 6/2014 | Pham et al. | |

FOREIGN PATENT DOCUMENTS

| | | |
|---|---|---|
| CA | 2346912 A1 | 4/2000 |
| EP | 1352616 A1 | 10/2003 |
| GB | 1175498 A | 12/1969 |

(Continued)

*Primary Examiner* — James C Yager
*Assistant Examiner* — Thomas J Kessler
(74) *Attorney, Agent, or Firm* — Muncy, Geissler, Olds & Lowe, P.C.

(57) ABSTRACT

The present invention relates to an elastomeric composition, wherein the elastomeric composition comprises an additive selected from any one or a combination of fluorine and silicone compounds in the production of a hypoallergenic elastomeric article.

5 Claims, No Drawings

(56) References Cited

FOREIGN PATENT DOCUMENTS

| WO | WO 1992013497 A1 | 8/1992 | |
|----|------------------|--------|---|
| WO | WO 2000/009590 | 2/2000 | |
| WO | WO 2001/078620 | 10/2001 | |
| WO | WO 2003/057750 | 7/2003 | |
| WO | WO-2016175954 A2 * | 11/2016 | ................ C08L 9/04 |

* cited by examiner

ELASTOMERIC COMPOSITION FOR AN ELASTOMERIC ARTICLE

TECHNICAL FIELD OF THE INVENTION

The disclosure relates to an elastomeric composition for producing a hypoallergenic elastomeric article.

BACKGROUND OF THE INVENTION

The discovery of natural latex from the sap of the *Hevea brasilisensis* tree has since paved the way for a blooming rubber industry. Some examples of commercialised natural latex products include gloves, condoms, balloons, or pacifiers.

However, it was discovered that latex proteins, present in natural latex, could cause allergic reactions. Traces of latex proteins remain present in any products made from natural latex, resulting in those with a developed sensitivity to said latex proteins to break out in hives, rashes, or itchiness when in contact with the product. Additionally, certain products made from natural latex such as gloves or balloons may contain a powder which carries the latex protein. When inhaled, these individuals could also have difficulty with breathing. In severe cases, anaphylactic shock may occur.

Unfortunately, the adverse effects of latex proteins are not only confined to individuals with a latex allergy. Rather, those with an ongoing exposure to latex products may develop dermatitis on the area of contact, causing the skin on the area of contact to be rough and dry. Indeed, latex proteins may also be absorbed through broken or damaged skin, and those continuously exposed to latex products are at a higher risk of developing an allergy (Australasian Society of Clinical Immunology and Allergy 2010; American College of Allergy, Asthma & Immunology 2014).

With prolonged exposure, the adverse effects of latex proteins have the potential to affect just about anyone, regardless of whether or not the individual is allergic. An example of a group of people that are more likely to be affected by said problems are those in the medical or research field, as they are constantly required to wear latex gloves for protection against contamination, harsh chemicals, or dangerous pathogens.

As a result, alternative solutions have been proposed to overcome this limitation of latex products, and in particular, this limitation in latex gloves. One method for hypoallergenic latex gloves includes a chlorination process in the production of the latex glove, where the glove is dipped in chlorine to remove or break down the latex protein present in the latex glove as demonstrated in WO 1992013497 and U.S. Pat. No. 6,391,409. However, this process is not without risks, as it was discovered that chlorination of a latex glove could decrease the shelf-life, strength, or elasticity of the product, compromising the quality of the natural latex glove altogether.

A second approach to overcoming this limitation was then to make the switch from natural latex to synthetic latex, which has characteristics similar to natural latex but lacks the actual latex protein itself. In this process, polymer chains crosslink during vulcanisation, with sulphur typically acting as the cross-linking component in the polymer chain. Additionally, chemical accelerators and activators are added to assist with the speed of binding between sulphur and the polymer chain.

Synthetic latex is especially favoured in the medical field, as conventional synthetic latex gloves offer users the option of a comfortable glove thin enough so that their dexterity or ability to maintain accurate control over their instruments for a long period of time is unaffected, but yet provides the users with the required protective barrier usually only offered by other thicker, bulkier gloves.

Products made from synthetic latex are well known in the field, and CA 2346912 and EP 1352616 are two examples of a wide selection of documents that disclose the use of sulphur, accelerators, and activators in the composition and method for producing synthetic latex gloves. However, a number of drawbacks occur when said additives of sulphur, accelerators, and activators are added to the latex composition. Particularly, chemical residues from the accelerators may be present in any synthetic latex products made therefrom, which have been discovered to be able to potential irritants which may trigger an antigenic response, e.g. chronic dermatitis, when in contact with individuals. At the same time, traces of these additives may remain present in the synthetic latex glove made therefrom, and can be potential contaminants. As a result, despite lacking the latex protein, these synthetic latex gloves produced accordingly may still cause an antigenic response in individuals.

There is thus is a need for an elastomeric composition for an elastomeric article which addresses the limitations as discussed above.

SUMMARY OF THE INVENTION

An objective of the invention is to therefore provide an elastomeric composition for an elastomeric article which reduces the possibility of causing an antigenic response in its users.

Another objective of the present invention is to provide an elastomeric composition which does not comprise sulphur, activators, or accelerators so that elastomeric articles produced therefrom would not contain the same.

Yet another objective of the invention is to provide an elastomeric composition for producing an elastomeric article with improved resistive properties for functioning as a protective barrier.

These and other objectives of the invention are achieved through an elastomeric composition for producing an elastomeric article as disclosed herein. More particularly, the elastomeric composition comprises an elastomer and an additive selected from any one or a combination of fluorine or silicone compounds, which bond to the chains of the elastomer. The elastomeric composition may also comprise of a surfactant and an antioxidant.

Advantageously, the elastomeric article produced therefrom is hypoallergenic, which consequently reduces the possibility of causing an antigenic response in its users.

DETAILED DESCRIPTION OF THE INVENTION

Embodiments of the present invention will now be described in a more detailed manner, and the scope of the invention will be fully conveyed to those skilled in the art. However, it should be understood that the present disclosure is not intended to limit the invention to the precise forms as disclosed, but rather, provided so that the disclosure will be thorough and complete.

The present invention relates to an elastomeric composition for producing an elastomeric article. More specifically, it relates to an elastomeric composition comprising an elastomer and an additive for producing the elastomeric article, where the additive is selected from any one or a combination of fluorine or silicone compounds which bond with the chains of the elastomer in the elastomeric composition.

Advantageously, the elastomeric article produced according to the elastomeric composition is hypoallergenic.

The elastomeric article as discussed hereon forth in the disclosure will be in reference to a latex glove, although it shall not be limited to as such.

In the embodiment of the present invention, the elastomer utilised in the elastomeric composition comprises about 18 wt. % of total solid content (TSC) of latex. However, it will be appreciated that the TSC of latex present in the elastomeric composition may be modified accordingly based on the type and function of the elastomeric article produced.

In the first embodiment, the elastomeric composition comprises the elastomer and the additive, wherein the additive is the fluorine compound. The fluorine compound is a fluorocarbon, and the fluorocarbon preferably comprises of 6 or fewer carbon atoms. Further, the fluorine compound is preferably unable to be broken down to form perfluorooctanoic acid (PFOA) or perfluorooctanesulfonic acid (PFOS).

The fluorocarbon is preferably tetrafluoroethylene with the chemical formula $C_2F_4$.

Alternatively, the fluorocarbon can either be in the form of an aqueous dispersion or aqueous emulsion. The fluorocarbon can also either be anionic or non-ionic.

The fluorine compound in the elastomeric composition has a concentration range from 0.1 wt. % to 30 wt. %.

Given the concentration range of the fluorine compound in the elastomeric composition, it should be noted that the concentration of the fluorine compound in the elastomeric composition is dependent on the thickness and functionality of the elastomeric article intended to produce. The higher the concentration of the fluorine compound in the elastomeric composition for example, the more resistant the elastomeric article produced will be, i.e. a higher resistance to heat, chemicals, or water. To elaborate a further example, a higher concentration of fluorine compound is required in the elastomeric composition for the production of a work glove, as compared to the concentration of fluorine compound in the elastomeric composition for the production of a surgical glove.

In reference to the present embodiment, the elastomeric composition comprises a concentration of 9 wt. % of fluorine compound when the TSC of latex in the elastomeric composition is 18 wt. % in the production of a surgical glove.

The concentration of fluorine compound in the elastomeric composition may therefore be modified accordingly within the range from 0.1 wt. % to 30 wt. %.

Given the high electronegativity of the electron configuration of fluorine, the fluorine compound is therefore able to easily bond with the polymer chains of the elastomer in the present embodiment to give rise to a stable elastomeric composition.

Advantageously, the elastomeric composition according to the first embodiment is able to produce an elastomeric article with an improved resistance to heat, chemicals, and water, the results which will be discussed below herein.

It should be highlighted that a key feature of the present invention is that the elastomeric composition does not require the addition of sulphur, an activator, or an accelerator. Both sulphur and the activator may be potential contaminants in any latex gloves made therefrom. For example, sulphur particles present in the latex glove could cause discolouration, especially when it comes in contact with traces of metal. This is especially unavoidable in the presence of the activator, with the most known activator to be zinc oxide. Additionally, it should also be noted that any traces of zinc oxide on the latex glove is especially undesirable when the latex glove is donned during the handling of food products. On the other hand, the accelerator, such as thiurams, mercaptobenzothiazole, carbamates, or any of their derivatives can be potential irritants that could cause chronic dermatitis in users. Without the presence of these additives in the present embodiment, the elastomeric article produced according to the present embodiment may avoid the negative effects associated with said additives. The elastomeric article is therefore advantageous over conventional elastomeric articles in this regard.

To elaborate further, another favourable feature of the elastomeric composition as disclosed is that the elastomeric composition of the present embodiment is environmentally friendly and safe. The fluorine compound utilised in the present invention does not comprise more than 6 carbons, which has been chosen by the inventors to decrease carbon footprint. Further, the fluorine compound also cannot be broken down into PFOA and PFOS, which is extremely beneficial to the environment as PFOA and PFOS are resistant to environmental degradation processes. The toxicity and bioaccumulation of PFOS and PFOA therefore have the potential to be extremely harmful to the environment.

It is also highlighted that the absence of zinc oxide as the activator in the present application is an added benefit, as it does not contribute to earth pollution.

According to a second embodiment of the invention, the elastomeric composition may comprise the elastomer and a combination of the fluorine compound and the silicone compound.

The silicone compound is a polysiloxane. Given the low surface energy of polysiloxane, the addition of the silicone compound to the elastomeric composition provides any elastomeric article produced therefrom with an improved layer of protective barrier against water, chemicals, or heat. In the present embodiment, the polysiloxane is reacted with an organic polyether comprising both ethylene oxide and propylene oxide groups to produce a modified silicone emulsion. The amount of ethylene oxide and propylene oxide groups in the modified silicone emulsion is such that there is a sufficient amount of ethylene oxide present in the modified silicone emulsion which allows for a large number of water molecules to be semi-attached via hydrogen bonds to the ethylene oxide. As a result, the ethylene oxide present in the modified silicone emulsion provides the silicone compound with water solubility, pro-foaming, and wetting properties. On the other hand, the propylene oxide provides oil solubility, de-foaming properties, and de-aeration properties in the modified silicone emulsion. Overall, the silicone compound as modified herein provides good film formation, low interfacial tension, de-foaming, and quick drying properties which beneficially speeds up the overall process in the production of any elastomeric article produced therefrom, being a glove in this embodiment of the invention.

The concentration of the silicone compound in the elastomeric composition is dependent on the concentration of TSC of latex present in the elastomeric composition. As such, the concentration of silicone compound in the elastomeric composition may vary between 0.1 wt. % to 5 wt. %.

Similar to the first embodiment, the concentration of TSC of latex present in the elastomeric composition may vary depending on the type and function of the elastomeric article intended to produce. Nevertheless, assuming the TSC of latex remains at a concentration of 18 wt. %, the concentration of fluorine compound in this embodiment is 9 wt. %, while the concentration of silicone compound is 0.49 wt. % in the production of a latex surgical glove.

The fluorine compound is as described herein above, which is a tetrafluoroethylene.

The elastomeric composition may also comprise a surfactant. As the surfactant functions to lower the surface energy between the elastomer and the silicone compound in the elastomeric composition, the concentration of the surfactant may therefore be modified depending on the concentration of the silicone compound. A higher concentration of silicone compound present in the elastomeric composition causes the elastomeric composition to be less stable. The addition of surfactant therefore stabilises the elastomeric composition, and should be added in concentrations ranging from 0.1 wt. % to 3.5 wt. %.

In the present embodiment, an amount of 0.19 wt. % in concentration of surfactant is added to the elastomeric composition when the silicone compound is 0.49 wt. % in concentration.

The surfactant can be selected from any one of an anionic surfactant, a non-ionic surfactant, or a cationic surfactant.

The elastomeric article is also hypoallergenic, and therefore, reduces the possibility of causing an antigenic reaction in users.

Further disclosed is a third embodiment of the present invention.

The elastomeric composition according to this embodiment comprises of the elastomer, the silicone compound, and surfactant.

In this embodiment, the silicone compound and the surfactant remain the same as discussed herein above, that is, a polysiloxane reacted with organic polyether comprising both ethylene oxide and propylene oxide, and a surfactant selected from any one of an anionic surfactant, a non-ionic surfactant, or a cationic surfactant.

Additionally, in this embodiment, the concentration ranges of the silicone compound and surfactant in the elastomeric composition remain the same, that is, with a concentration range of 0.1 wt. % to 5 wt. % and 0.1 wt. % to 3.5 wt. % respectively.

Again, as disclosed herein above, the concentration of TSC of latex in the elastomeric composition may again vary depending on the function and type of elastomeric article produced. However, assuming that the intended latex article is a surgical glove, the concentration of TSC of latex remains at 18 wt. %. With the concentration of TSC of latex at 18 wt. %, the concentration of silicone compound is 0.49 wt. % whilst the surfactant has a concentration of 0.19 wt. %.

The invention according to the third embodiment may also comprise the addition of an antioxidant, which helps stabilise the elastomeric composition by inhibiting oxidation in the elastomeric composition.

As the concentration of antioxidant in the elastomeric composition is dependent on the concentration of TSC of latex in the elastomeric composition, the concentration range of the antioxidant may vary from 0.1 wt. % to 5 wt. %.

In the present embodiment, the concentration of antioxidant in elastomeric composition is 0.49 wt. % when the concentration of TSC of latex is 18 wt. %.

The antioxidant in the present embodiment can be selected from any one of phenolic, phosphite, or amine antioxidants, or antioxidants not listed herein which assists in preventing the degradation of latex articles.

However, it will be appreciated that the addition of antioxidant in the present embodiment is optional.

It is important to highlight again that the first, second, and third embodiments of the present invention do not comprise sulphur, an activator, or any accelerators. As such, any elastomeric article produced would lack any traces of the additives as well as the effects associated with the additives.

Furthermore, the absence of zinc oxide as the activator in the embodiments is an added benefit, as it does not contribute to earth pollution.

The elastomer utilised in the embodiments of the present invention can be selected from any one of polyurethane, acrylonitrile rubber, polychloroprene, synthetic polyisoprene, styrene isoprene styrene, styrene ethylene butadiene styrene, or natural rubber. It is preferred, however, that the elastomer utilised in the elastomeric composition is polyurethane.

Using a dipping method, the inventor demonstrates the production of gloves according to the elastomeric composition of the first, second, and third embodiments. In these examples, the gloves were produced using elastomers comprising polyurethane, acrylonitrile rubber, polychloroprene rubber, synthetic polyisoprene, or natural rubber.

The surfactant added to the elastomeric composition in the production of the gloves in this example is sodium dodecylbenzene sulfonate, while the antioxidant is a butylated reaction product of p-cresol and dicyclopentadiene. The process flow of the production of gloves is detailed in table 1 below.

TABLE 1

Process parameters for producing a polyurethane (PU), polychloroprene (CR), synthetic polyisoprene (PI), acrylonitrile butadiene rubber (NBR), or natural rubber (NR) latex glove

| | PU/CR/PI/NBR/NR glove glove process flow | | | | | |
| --- | --- | --- | --- | --- | --- | --- |
| Process flow | Temp (° C.) | Dwell time (Second) | Concentration (%) | pH Value | Water flow rate (LPM) | Viscosity Cps-spinder 1, 60 rpm, 25° C. |
| 1)former cleaning a)Option 1 | | | | | | |
| 1)Acid | 35~60 | 3~8 | 1.5~4 | 2~4 | 2~3 | |
| 2)Base | 35~60 | 8~20 | 4~8 | 10~14 | 2~3 | |
| 3)Rinse - Clean water | 55~70 | 10~15 | | 7~9.5 | 3~15 | |
| b)Option 2 | | | | | | |
| 1)Surfactant | 60~80 | 20~40 | 2~4 | 6~8 | 2~3 | |
| 2)Rinse - Clean water | 55~70 | 10~15 | | 7~9.5 | 3~15 | |

TABLE 1-continued

Process parameters for producing a polyurethane (PU), polychloroprene (CR), synthetic polyisoprene (PI), acrylonitrile butadiene rubber (NBR), or natural rubber (NR) latex glove

| Process flow | PU/CR/PI/NBR/NR glove glove process flow | | | | | |
|---|---|---|---|---|---|---|
| | Temp (° C.) | Dwell time (Second) | Concentration (%) | pH Value | Water flow rate (LPM) | Viscosity Cps-spinder 1, 60 rpm, 25° C. |
| 2)Coagulant Dipping Tank | | | | | | |
| a)Option 1 | 40~60 | 12~21 | | 6~8.5 | | 4~9 |
| 1)Wetting agent | | | 0.05~3 | | | |
| 2)Calcium Nitrate/Calcium Chloride | | | 5~20 | | | |
| a)Option 2 | 40~60 | 12~21 | | 6~8.5 | | 4~9 |
| 1)Metalic Stearic - Zinc, Cal, K, Mg | | | 0.5~3 | | | |
| 2)Wetting agent | | | 0.05~3 | | | |
| 3)Calcium Nitrate/Calcium Chloride | | | 5~20 | | | |
| b)Option 3 | 40~60 | 12~21 | | 7~9.5 | | 4~9 |
| Calcium carbonate | | | 3~8 | | | |
| Wetting agent | | | 0.05~3 | | | |
| Calcium Nitrate/Calcium Chloride | | | 5~20 | | | |
| 3)Coagulant Oven - Infra ray/Hot air/Far infra ray | 80~140 | 90~150 | | | | |
| 4) Latex dipping tank | | | | | | |
| a)Option 1 - Single dipping | 25~38 | 14~30 | 14~40 | 6~8 | | 3~10 |
| b)Option 2 - Double dipping | | | | | | |
| First Dipping | 25~38 | 14~30 | 14~40 | 6~8 | | 3~10 |
| Drying Oven - Infra Ray/Hot air/Far infra ray | 60~120 | 30~150 | | | | |
| Second Dipping | 25~38 | 14~30 | 14~40 | 6~8 | | 3~10 |
| 4)Gelling Oven - Infra Ray/Hot air/Far infra ray | 60~120 | 30~150 | | | | |
| 5)Pre Leaching - Clean Water | 40~80 | 60~160 | | | 20~100 | |
| 6)Donning Surface coating - PUD/PA/Flourine | 20~40 | 5~15 | 0.5~3 | 5~10 | | 3~10 |
| 7)Polymer Drying Oven - Infra Ray/Hot air/Far infra ray | 60~120 | 30~150 | | | | |
| 8)Beading Station | | | | | | |
| 9)Drying&Curing Oven - Infra Ray/Hot air/Far infra ray | 80~150 | 600~1200 | | | | |
| 10)Post Leaching - Clean Water | 40~80 | 60~160 | | | 20~100 | |
| 11)Cooling - Clean Water | | | | | | |
| 12)Chlorination | | | | | | |
| 13)Neutralizer | | | | | | |
| 14)Rinse | | | | | | |
| 15)Donning Coating - Optional | | | | | | |
| Option 1 - Calcium Carbonate/Constuch | 30~50 | 5~8 | 3~8 | 9~10 | | 3~10 |
| Option 2 - Moisturizer (Plants/Fruit/Vege active/etc) | 25~35 | 5~8 | 1~5 | 5~8 | | 3~10 |
| Option 3 - chlorofluorocarbons (CFCs) | 25~35 | 5~8 | 0.5~5 | 5~8 | | 3~10 |
| 16)Drying Oven - Infra Ray/Hot air/Far infra ray | 80~150 | 120~240 | | | | |
| 17)Stripping station - Manual/Auto Striping | | | | | | |
| 18)Collecting glove - Manual/Auto Stripping | | | | | | |

TABLE 2

Process parameters for producing a synthetic polyisoprene (PI), acrylonitrile butadiene rubber (NBR), or natural rubber (NR) latex glove

| Process flow | PI/NR/NBR glove process flow | | | | | |
|---|---|---|---|---|---|---|
| | Temp (° C.) | Dwell time (second) | Concentration (%) | pH Value | Water flow rate (LPM) | Viscosity Cps - spinder 1, 60 rpm, 25° C. |
| 1)former cleaning | | | | | | |
| a)Option 1 | | | | | | |
| 1)Acid | 35~60 | 3~8 | 1.5~4 | 2~4 | 2~3 | |
| 2)Base | 35~60 | 8~20 | 4~8 | 10~14 | 2~3 | |
| 3)Rinse - Clean water | 55~70 | 10~15 | | 7~9.5 | 3~15 | |
| b)Option 2 | | | | | | |
| 1)Surfactant | 60~80 | 20~40 | 2~4 | 6~8 | 2~3 | |
| 2)Rinse - Clean water | 55~70 | 10~15 | | 7~9.5 | 3~15 | |
| 2)Coagulant Dipping Tank | | | | | | |
| a)Option 1 | 40~60 | 12~21 | | 6~8.5 | | 4~9 |
| 1)Wetting agent | | | 0.05~3 | | | |
| 2)Calcium Nitrate/Calcium Chloride | | | 5~20 | | | |

TABLE 2-continued

Process parameters for producing a synthetic polyisoprene (PI), acrylonitrile butadiene rubber (NBR), or natural rubber (NR) latex glove

| Process flow | PI/NR/NBR glove process flow | | | | | |
|---|---|---|---|---|---|---|
| | Temp (° C.) | Dwell time (second) | Concentration (%) | pH Value | Water flow rate (LPM) | Viscosity Cps - spinder 1, 60 rpm, 25° C. |
| a)Option 2 | 40~60 | 12~21 | | 6~8.5 | | 4~9 |
| 1)Metalic Stearic - Zinc, Cal, K, Mg | | | 0.5~3 | | | |
| 2)Wetting agent | | | 0.05~3 | | | |
| 3)Calcium Nitrate/Calcium Chloride | | | 5~20 | | | |
| b)Option 3 | 40~60 | 12~21 | | 7~9.5 | | 4~9 |
| Calcium carbonate | | | 3~8 | | | |
| Wetting agent | | | 0.05~3 | | | |
| Calcium Nitrate/Calcium Chloride | | | 5~20 | | | |
| 3)Coagulant Oven - Infra ray/Hot air/Far infra ray | 80~140 | 90~150 | | | | |
| 4)Latex dipping tank | | | | | | |
| a)Option 1 - Single dipping | 25~38 | 14~30 | 14~40 | 6~8 | | 3~10 |
| b)Option 2 - Double dipping | | | | | | |
| First Dipping | 25~38 | 14~30 | 14~40 | 6~8 | | 3~10 |
| Drying Oven - Infra Ray/Hot air/Far infra ray | 60~120 | 30~150 | | | | |
| Second Dipping | 25~38 | 14~30 | 14~40 | 6~8 | | 3~10 |
| 4)Gelling Oven - Infra Ray/Hot air/Far infra ray | 60~120 | 30~150 | | | | |
| 5)Pre Leaching - Clean Water | 40~80 | 60~160 | | | 20~100 | |
| 6)Donning Surface coating - PUD/PA/Flourine | 20~40 | 5~15 | 0.5~3 | 5~10 | | 3~10 |
| 7)Polymer Drying Oven - Infra Ray/Hot air/Far infra ray | 60~120 | 30~150 | | | | |
| 8)Beading Station | | | | | | |
| 9)Drying&Curing Oven - Infra Ray/Hot air/Far infra ray | 80~150 | 600~1200 | | | | |
| 10)Post Leaching - Clean Water | 40~80 | 60~160 | | | 20~60 | |
| 11)Cooling - Clean Water | 30~50 | 10~20 | | | 10~20 | |
| 12)Chlorination | 25~30 | 20~40 | 0.05~0.12 | | | |
| 13)Neutralizer | 30~50 | 8~20 | | 6~8 | 5~10 | |
| 14)Rinse | 40~80 | 25~40 | | | 20~60 | |
| 15)Donning Coating - Optional | | | | | | |
| Option 1 - Calcium Carbonate/Constuch | 30~50 | 5~8 | 3~8 | 9~10 | | 3~10 |
| Option 2 - Moisturizer (Plants/Fruit/Vege active/etc) | 25~35 | 5~8 | 1~5 | 5~8 | | 3~10 |
| Option 3 - chlorofluorocarbons (CFCs) | 25~35 | 5~8 | 0.5~5 | 5~8 | | 3~10 |
| 16)Drying oven - Infra Ray/Hot air/Far infra ray | 80~150 | 120~240 | | | | |
| 17)Stripping station - Manual/Auto Striping | | | | | | |
| 18)Collecting glove - Manual/Auto Stripping | | | | | | |

It should be noted that the key difference between Table 1 and Table 2 is that beneficially, a chlorination step (step 12 in the tables above) is not required when the elastomer in the elastomeric composition is polyurethane or polychloroprene.

Then, the produced gloves were subjected to various tests to determine the physical properties of aged and unaged gloves, as well as the chemical resistance of the gloves. The results for the polyurethane gloves (labelled INOV8-V3, INOV8-V4, and INOV8-V5 below) produced according to the first, second, and third embodiment are shown below. A control (labelled INOV8-V1) comprising of polyurethane without any additives was also produced according to the process parameter above.

Results

TABLE 3

| Physical properties of aged and unaged gloves | | | | | | | |
|---|---|---|---|---|---|---|---|
| | ASTM - D3577 | | | | | Tear Resistance | EN 455 -2 Force |
| Product Type | Tensile Strength, MPa | M100, MPa | M300, MPa | M500, MPa | EAB, % | (Initial), kN/m | at Break, N |
| Initial - Unaged gloves Non Irradiated - Non Sterile | | | | | | | |
| INOV8 - V1 | 21-28 | 0.8-1.0 | 1.5-1.8 | 2.3-2.8 | 920-1000 | 22-24 | 8.8-11 |
| INOV8 - V3 | 25-35 | 1.1-1.4 | 1.7-2.0 | 2.8-3.30 | 890-1000 | 25-28 | 9.5-12 |
| INOV8 - V4 | 21-30 | 1.3-1.6 | 1.8-2.2 | 3-3.8 | 900-980 | 23-26 | 8.5-10 |
| INOV8 - V5 | 22-32 | 1.3-1.8 | 1.7-2.3 | 2.7-3.6 | 920-1000 | 25-29 | 9.5-12 |
| Irradiated - Sterile | | | | | | | |
| INOV8 - V1 | N/A | N/A | N/A | N/A | N/A | N/A | N/A |
| INOV8 - V3 | 23-33 | 1.0-1.3 | 1.5-1.8 | 2.6-3.0 | 880-980 | 23-26 | 9.5-11 |
| INOV8 - V4 | 22-28 | 1.3-1.7 | 1.8-2.3 | 3.2-3.7 | 880-920 | 22-25 | 8.5-10 |
| INOV8 - V5 | 23-30 | 1.1-1.3 | 1.4-1.7 | 2.6-3.0 | 940-1000 | 23-28 | 9.0-12 |

TABLE 3-continued

Physical properties of aged and unaged gloves

| Product Type | ASTM - D3577 | | | | | Tear Resistance (Initial), kN/m | EN 455 -2 Force at Break, N |
|---|---|---|---|---|---|---|---|
| | Tensile Strength, MPa | M100, MPa | M300, MPa | M500, MPa | EAB, % | | |
| Aged 7 days @ 70° C. Non-Irradiated - Non Sterile | | | | | | | |
| INOV8 - V1 | Test piece melted | | | | | | |
| INOV8 - V3 | 25-37 | 1.0-1.3 | 1.7-2.1 | 2.8-3.20 | 890-980 | 24-27 | 9.5-12.5 |
| INOV8 - V4 | 22-32 | 1.1-1.4 | 1.4-1.8 | 2.6-3.4 | 930-1110 | 24-26 | 8.5-10 |
| INOV8 - V5 | 23-29 | 1.0-1.2 | 1.3-1.7 | 2.5-3.3 | 940-980 | 22-26 | 9.5-12 |
| Irradiated - Sterile | | | | | | | |
| INOV8 - V1 | N/A | N/A | N/A | N/A | N/A | N/A | n/a |
| INOV8 - V3 | 24-32 | 0.9-1.2 | 1.4-1.7 | 2.5-2.9 | 900-1100 | 22-25 | 8.5-10 |
| INOV8 - V4 | 20.5-29 | 1.1-1.5 | 1.4-1.8 | 2.6-2.9 | 930-1100 | 24-27 | 9.0-11 |
| INOV8 - V5 | 22-28 | 0.9-1.1 | 1.3-1.6 | 2.4-2.8 | 940-1000 | 22-25 | 9.5-11.5 |

Note:
INOV8 - V1 are gloves made from an elastomeric composition comprising polyurethane without any additives.
INOV8 - V3 are gloves made from an elastomeric composition comprising polyurethane (PU) and a silicone compound and antioxidant as the additives. The silicone compound is polysiloxane emulsion reacted with a mixture of modified ethylene oxide and propylene oxide, and the antioxidant is a phenolic compound obtained from a butylated reaction of p-cresol and dicyclopentadiene.
INOV8 - V4 are gloves made from an elastomeric composition comprising polyurethane (PU) and aqueous emulsions of fluorine compound as the additive. The aqueous emulsions of fluorine compound comprise a combination of different solid content and ionic characters.
INOV8 - V5 are gloves made from an elastomeric composition comprising polyurethane (PU) and aqueous emulsions of fluorine compound and silicone compound as the additives. The aqueous emulsions of fluorine compound comprise a combination of different solid content and ionic characters, and the silicone compound is a polysiloxane emulsion reacted with a mixture of modified ethylene oxide and propylene oxide.

As illustrated in the results above, the gloves produced according to the embodiments of the present invention were tested using the American Society for Testing and Materials (ASTM)-D3577 test.

The tensile strength of the unaged gloves with additives, i.e. INOV8-V3, INOV8-V4, INOV8-V5, fall within the range of 21-35 MPa, while the elongation at break percentage of the gloves fall within the range of 880-1000%, and the highest reading of the modulus 500 is 3.8 MPA.

Similarly, the aged gloves with additives, that is gloves aged for 7 days at 70° C., show promising results as well. The tensile strength for the aged gloves fall within the range of 20.5-37 MPa, while the elongation at break percentage of the gloves fall within the range of 890-1000%, and the highest reading of the modulus 500 is 3.4 MPa.

Further, it can also be seen from the results that the tear resistance of the gloves fall within the range of 23-29 kN/m for unaged gloves, and 22-27 kN/m for gloves aged for 7 days at 70° C., which indicates that the gloves are not easily torn, as a large force is required to tear the gloves.

Contrastingly, when subjected to the same test, the control, that is to say INOV8-V1 which does not comprise any additives, melted when it was aged for 7 days at 70° C. The minimum requirements for testing a glove are that the glove has to pass the unaged and aged test whilst non-sterilised. As the control did not pass the aged test, further tests were not necessary as it is evident that the glove could not offer sufficient protection to the user.

These results produced by the gloves according to the first, second, and third embodiments far exceed the minimum requirements as set forth by the ATSM test for latex gloves, and there is not a large deviation in results whether or not the gloves were aged, treated with heat, or sterilised. As such, the results therefore indicate that the gloves have an improvement in heat resistance, an improvement in shelf-life, and an overall improvement in quality and protection when the additives as disclosed in the embodiments of the invention are added to the glove, whether sterilised or unsterilized.

Chemical Resistance of PU Gloves

TABLE 4

Swelling Index of gloves (%)

| | | Time (Minutes) | | | | | | | | | | | | | | |
|---|---|---|---|---|---|---|---|---|---|---|---|---|---|---|---|---|
| | | 0 | 1 | 2 | 3 | 4 | 5 | 6 | 7 | 8 | 9 | 10 | 15 | 20 | 25 | 30 |
| ISO Propyl | V1 | 0 | 8 | 13 | 14 | 16 | 20 | 20 | 20 | 20 | 20 | 20 | 24 | 24 | 24 | 24 |
| Alcohol | V3 | 0 | 0 | 0 | 4 | 8 | 8 | 12 | 12 | 16 | 16 | 16 | 16 | 16 | 16 | 16 |
| | V4 | 0 | 12 | 16 | 20 | 20 | 20 | 20 | 20 | 20 | 20 | 20 | 20 | 20 | 20 | 20 |
| | V5 | 0 | 14 | 18 | 20 | 22 | 22 | 22 | 22 | 22 | 22 | 22 | 22 | 22 | 22 | 22 |
| Toluene | V1 | 0 | 48 | 60 | 68 | 72 | 76 | 76 | 76 | 76 | 76 | 76 | 76 | 76 | 76 | 76 |
| | V3 | 0 | 56 | 64 | 68 | 72 | 72 | 72 | 72 | 72 | 76 | 76 | 76 | 76 | 76 | 76 |
| | V4 | 0 | 44 | 52 | 56 | 56 | 56 | 56 | 56 | 56 | 56 | 56 | 60 | 60 | 60 | 60 |
| | V5 | 0 | 40 | 56 | 60 | 60 | 60 | 60 | 60 | 60 | 60 | 60 | 62 | 62 | 62 | 62 |
| Acetonitrile | V1 | 0 | 28 | 36 | 44 | 44 | 44 | 44 | 44 | 44 | 44.8 | 44.8 | 45 | 60 | 60 | 68 |
| | V3 | 0 | 36 | 40 | 40 | 40 | 40 | 40 | 40 | 40 | 40 | 40 | 40 | 40 | 40 | 40 |
| | V4 | 0 | 44 | 44 | 44 | 44 | 44 | 44 | 44 | 44 | 44 | 44 | 44 | 44 | 44 | 44 |
| | V5 | 0 | 40 | 40 | 40 | 40 | 40 | 40 | 40 | 40 | 40 | 40 | 40 | 40 | 40 | 40 |
| NaOH 50% | V1 | 0 | 0 | 0 | 0 | 0 | 0 | 0 | 0 | 0 | 0 | 0 | 0 | 0 | 0 | 0 |
| | V3 | 0 | 0 | 0 | 0 | 0 | 0 | 0 | 0 | 0 | 0 | 0 | 0 | 0 | 0 | 0 |
| | V4 | 0 | 0 | 0 | 0 | 0 | 0 | 0 | 0 | 0 | 0 | 0 | 0 | 0 | 0 | 0 |
| | V5 | 0 | 0 | 0 | 0 | 0 | 0 | 0 | 0 | 0 | 0 | 0 | 0 | 0 | 0 | 0 |

TABLE 4-continued

Swelling Index of gloves (%)

| | | Time (Minutes) | | | | | | | | | | | | | | |
|---|---|---|---|---|---|---|---|---|---|---|---|---|---|---|---|---|
| | | 0 | 1 | 2 | 3 | 4 | 5 | 6 | 7 | 8 | 9 | 10 | 15 | 20 | 25 | 30 |
| Acetone | V1 | 0 | 60 | 80 | 80 | 84 | 84 | 84 | 88 | 88 | 88 | 88 | 88 | 88 | 88 | 88 |
| | V3 | 0 | 60 | 68 | 76 | 76 | 76 | 76 | 76 | 80 | 80 | 80 | 84 | 84 | 84 | 84 |
| | V4 | 0 | 52 | 60 | 60 | 68 | 68 | 68 | 68 | 68 | 68 | 68 | 68 | 68 | 72 | 76 |
| | V5 | 0 | 56 | 62 | 72 | 72 | 72 | 72 | 72 | 72 | 72 | 72 | 72 | 72 | 74 | 78 |
| MEK | V1 | 0 | 84 | 92 | 108 | 108 | 108 | 112 | 116 | 116 | 116 | 116 | 116 | 116 | 116 | 116 |
| | V3 | 0 | 64 | 88 | 100 | 108 | 108 | 108 | 108 | 108 | 108 | 112 | 112 | 112 | 112 | 112 |
| | V4 | 0 | 68 | 76 | 84 | 84 | 84 | 88 | 88 | 88 | 88 | 88 | 92 | 92 | 92 | 92 |
| | V5 | 0 | 66 | 78 | 88 | 88 | 88 | 94 | 94 | 94 | 94 | 94 | 96 | 96 | 96 | 96 |
| Ethanol | V1 | 0 | 15 | 20 | 24 | 28 | 28 | 28 | 28 | 28 | 28 | 28 | 28 | 28 | 28 | 28 |
| | V3 | 0 | 8 | 12 | 16 | 20 | 20 | 20 | 20 | 20 | 20 | 20 | 20 | 20 | 20 | 20 |
| | V4 | 0 | 16 | 20 | 20 | 20 | 20 | 20 | 20 | 20 | 20 | 20 | 20 | 20 | 20 | 20 |
| | V5 | 0 | 12 | 15 | 22 | 22 | 22 | 22 | 22 | 22 | 22 | 22 | 22 | 22 | 22 | 22 |
| DCM | V1 | | | | | | | | | | | | | | | |
| | V3 | 0 | 124 | 140 | 148 | 156 | 164 | 164 | 168 | 172 | 172 | 172 | 184 | 188 | 192 | 196 |
| | V4 | 0 | 104 | 105 | 124 | 128 | 140 | 140 | 140 | 140 | 140 | 140 | 140 | 140 | 140 | 144 |
| | V5 | 0 | 118 | 126 | 126 | 132 | 150 | 150 | 150 | 150 | 150 | 150 | 150 | 150 | 150 | 160 |

Note:
V1 are gloves made from an elastomeric composition comprising polyurethane without any additives.
V3 are gloves made from an elastomeric composition comprising polyurethane (PU) and a silicone compound and antioxidant as the additives. The silicone compound is polysiloxane emulsion reacted with a mixture of modified ethylene oxide and propylene oxide, and the antioxidant is a phenolic compound obtained from a butylated reaction of p-cresol and dicyclopentadiene.
V4 are gloves made from an elastomeric composition comprising polyurethane (PU) and aqueous emulsions of fluorine compound as the additive. The aqueous emulsions of fluorine compound comprise a combination of different solid content and ionic characters.
V5 are gloves made from an elastomeric composition comprising polyurethane (PU) and aqueous emulsions of fluorine compound and silicone compound as the additives. The aqueous emulsions of fluorine compound comprise a combination of different solid content and ionic characters, and the silicone compound is a polysiloxane emulsion reacted with a mixture of modified ethylene oxide and propylene oxide.

The chemical resistance of the V1, V3, V4, and V5 gloves was tested by immersing the gloves in chemicals such as isopropyl alcohol, toluene, acetonitrile, sodium hydroxide (NaOH 50%), acetone, methyl ethyl ketone (MEK), ethanol, and dichloromethane (DCM) for 30 minutes at room temperature to measure its swelling index (%). The formula below, $$Q = \frac{W_2 - W_1}{W_1}$$

is used to measure the swelling index (%) of the gloves, wherein Q is the swelling index (%), $W_1$ is the initial weight and $W_2$ is the swollen weight after being immersed in the chemicals for 30 minutes at room temperature. The lower the value of the swelling index (%), the more resistant the glove is to the chemicals over time.

As seen in Table 4, the final swelling index (%) readings of the V3, V4, and V5 gloves immersed in the chemicals over 30 minutes are lower compared to the V1 glove, apart from toluene, where the V3 glove had the same swelling index (%) as the V1 glove. The lower swelling index (%) overall of the V3, V4, and V5 gloves indicates that there is an increase in resistance towards said chemicals when the additives as disclosed in the present invention is added to the elastomeric composition in the production of the glove.

It is therefore clear based on the provided results that a glove produced according to any of the embodiments above not only meet standard ATSM requirements, but also shows significant improvement compared to a glove without any of the additives as disclosed herein.

Additionally, the walls of the V3, V4, and V5 gloves produced were as thin as 0.13 mm, 0.075 mm, and 0.11 mm respectively, which is especially favourable for surgical gloves for example, as users are able to don the gloves without having the gloves impair finger movement or control over a medical instrument. Furthermore, given the thin walls of the glove, the user is does not required to exert additional force to control said medical instrument when the glove is worn.

Yet despite the thin walls of the gloves, the gloves are still able to act as an effective barrier and provide optimum protection towards its user.

Preferably, the first and second embodiments of the present invention are most preferred, as the gloves produced according to those embodiments, gloves V4 and V5 respectively, were found to show the most promising results overall when tested, especially against chemical resistance.

Advantageously, the elastomeric compositions according to the embodiments of the present invention are able to produce a hypoallergenic glove with a reduced risk of triggering an antigenic response in users. The lack of any traces of activators, sulphur, or accelerator particles in the elastomeric compositions further contribute to this advantage, as well as decreases the possibility of contamination by chemical particles when the glove is donned.

The elastomeric composition of the embodiments above may also be used in the production of a condom, a dental dam or a balloon.

Additionally, the elastomeric composition may also be used as a coating for medical devices.

The present invention has therefore been described in specific embodiments in the above description. It should, however, be understood that the above description does not limit the invention to the above given details. It will be apparent to those skilled in the art that various changes and modification may be made therein without departing from the principle of the invention or from the scope of the appended claims.

REFERENCES

Australasian Society of Clinical Immunology and Allergy 2010, *Latex allergy*, accessed 30 Sep. 2016, <https://goo.gl/QLdtVn>

American College of Allergy, Asthma & Immunology 2014, *Latex allergy*, accessed 30 Sep. 2016, <https://goo.gl/LDqgHG>

The invention claimed is:

1. An elastomeric composition comprising:
   an elastomer;
   a surfactant;
   a phenolic antioxidant, and
   additives,
   wherein the elastomer comprises polyurethane having a concentration of 58.5 to 99.6 wt. %;
   the surfactant comprises sodium dodecylbenzene sulfonate having a concentration of 0.1 wt. % to 3.5 wt. %,
   the phenolic antioxidant has a concentration of 0.1 wt. % to 3 wt. %,
   the additives comprise tetrafluoroethylene and polysiloxane reacted with ethylene oxide and propylene oxide,
   the tetrafluoroethylene has a concentration of 0.1 wt. % to 30 wt. % and the polysiloxane has a concentration of 0.1 wt. % to 5 wt. %, which bond with the chains of the elastomer to produce a hypoallergenic elastomeric article with improved physical properties and chemical resistance.

2. The elastomeric composition according to claim 1, wherein the polysiloxane is an emulsion.

3. The elastomeric composition according to claim 1, wherein the elastomeric composition does not comprise activators, sulphur, or accelerators.

4. The elastomeric composition according to claim 1, wherein the elastomeric composition comprises elastomers selected from polyurethane, acrylonitrile rubber, polychloroprene, synthetic polyisoprene, styrene isoprene styrene, styrene ethylene butadiene styrene, or natural rubber.

5. The elastomeric composition according to claim 1, wherein the elastomeric article comprises a condom, a balloon, a dental dam, or a glove.

* * * * *